US005874083A

United States Patent [19]
Barnes et al.

[11] Patent Number: 5,874,083
[45] Date of Patent: Feb. 23, 1999

[54] IMMUNOPOTENTIATING COMPLEXES COMPRISING TRAT PROTEINS

[75] Inventors: Thomas Michael Barnes, Lane Cove; Philip Ralph Lehrbach, Wahroonga; Gregory John Russell-Jones, Middle Cove, all of Australia

[73] Assignee: Bioenterprises Pty Limited, East Roseville, Australia

[21] Appl. No.: 461,324

[22] Filed: Jun. 5, 1995

Related U.S. Application Data

[63] Continuation of Ser. No. 903,121, Jun. 23, 1992, abandoned, which is a continuation of Ser. No. 159,968, filed as PCT/AU87/00107 Apr. 16, 1987, abandoned.

[30] Foreign Application Priority Data

Apr. 21, 1986 [AU] Australia ................. PH5559
Mar. 13, 1987 [AU] Australia ................. PI0846

[51] Int. Cl.$^6$ ........................ A61K 39/385; A61K 39/295; A61K 39/40; A61K 39/42
[52] U.S. Cl. ......................... 424/193.1; 424/180.1; 424/192.1; 424/197.11; 435/69.1; 435/69.7; 530/402; 530/403
[58] Field of Search .................. 424/184.1, 180.1, 424/182.1, 193.1, 182, 197.1, 197.11; 435/69.1, 69.7; 530/402, 403

[56] References Cited

U.S. PATENT DOCUMENTS

| | | | |
|---|---|---|---|
| 4,336,336 | 6/1982 | Silhavy et al. | 435/172.3 |
| 4,356,170 | 10/1982 | Jennings et al. | 424/92 |
| 4,459,286 | 7/1984 | Hilleman et al. | 424/87 |
| 4,484,923 | 11/1984 | Amkraut et al. | 424/92 |
| 4,578,269 | 3/1986 | Morein | 424/88 |

FOREIGN PATENT DOCUMENTS

| | | | |
|---|---|---|---|
| 14506/83 | 11/1983 | Australia | C12N 15/00 |
| 32423/84 | 3/1985 | Australia | A61K 39/00 |
| 58943/86 | 1/1987 | Australia | C07K 7/08 |
| 0012078 | 6/1980 | European Pat. Off. | |
| 0055942 | 7/1982 | European Pat. Off. | |
| 055942 | 7/1982 | European Pat. Off. | C12N 15/00 |
| 0080806 | 6/1983 | European Pat. Off. | C12N 15/00 |
| 0094797 | 11/1983 | European Pat. Off. | |
| 0109688 | 5/1984 | European Pat. Off. | |
| 0138644 | 4/1985 | European Pat. Off. | |
| 0145359 | 6/1985 | European Pat. Off. | |
| 0146416 | 6/1985 | European Pat. Off. | G12N 15/00 |
| 0161188 | 11/1985 | European Pat. Off. | |
| 0180564 | 5/1986 | European Pat. Off. | |
| 0242243 | 10/1987 | European Pat. Off. | |
| 0243333 | 10/1987 | European Pat. Off. | C12N 15/02 |
| 2595374 | 9/1987 | France | C12N 15/00 |
| 2004744 | 4/1979 | United Kingdom | |
| 85 05122 | 11/1985 | WIPO | |
| 01212 | 2/1986 | WIPO | C07K 15/06 |
| 86 01212 | 2/1986 | WIPO | |

OTHER PUBLICATIONS

Derwent, Abstract Accession No. 86–176377/27.
G. Jung et al., "Potent B–lymphocyte Mitogens as Covalently Bound Carriers for the Presentation of Antigens and the Enhancement of Immune Response", Chemical Abstracts vol. 106, No. 1, Jan. 5, 1987, Abstract No. 3546a.
F. Zavala et al., "Rationale For Development of Synthetic Vaccine Against Plasmodium Falciparum Malaria", Science, vol. 228, Jun. 21, 1985, pp. 1436–1440.
B. Lugtenberg, "Purification of *Escherichia coli* OmpA Protein", Chemical Abstracts, vol. 105, No. 1, Jul. 7, 1986, p. 302, Abstract No. 3099m.
E. Minkley et al. "Overproduction Purification and Characterization of the F traT Protein", Chemical Abstracts, vol. 101, No. 21, Nov. 19, 1984, p. 170, Abstract No. 184976f.
G. Layton et al.,"The Effects of Oral and Combined Parenteral–Oral Immunization Against an Experimental *Escherichia Coli* Urinary Tract Infection in Mice",Biological Abstacts,vol. 77,No. 7, 1984, Abs. 541458.
U.K. Laemmli, "Cleavage of Structural Proteins During the Assembly of the Head of Bacteriophage T4", Nature, 227, (1970), 680–685.
I.E. Salit et al., "Intra–Strain Heterogencity of Gonococcal Pili is Related to Opacity Colony Variance" J. Exp. Med. 151, (1980), 716–725.
C.M. Tsai et al. "A Sentitive Silver Starin for Detecting Lipopolysaccharides in Polyacrylamides Gels", Analytical Biochemistry, 119, (1982), 115–119.
Little et al, "Preparation of Immunogenic 2.4 dinitrophyl & 2.46 Trinitrophenyl Proteins", *Methods in Immunology & Immunochemistry*, ed. C. Williams et al. Academic Press, New York, (1967), pp. 128–133.
S. Avrameas et al. "Coupling of a Enzymes to Antibodies and Antigens", Scand. J. Immunol., 8, Suppl. 7, (1978), pp. 7–23.
G. Russell–Jones et al. "Identification of Protein Antigens of Group B Streptococci with Special Reference to the 1bc Antigens", J. Exp. Med. 160, (1984), pp. 1476–1484.
R. Ogata et al."Nucleotide Sequence Analysis of the Complement Resistance Gene from Plasmid R100" J. Bacteriol., 151, 2, (1982), pp. 819–827.
M. Dyall–Smith et al. "Antigenic Determinants Coded by Rotavirus Genes", *Infectious Diarrhoea in the Young*, ed. TZIPORI, Elsevier Publishers, (1985), pp. 215–220.

(List continued on next page.)

*Primary Examiner*—Hazel F. Sidberry
*Attorney, Agent, or Firm*—Foley & Lardner

[57] ABSTRACT

Class of carrier molecules which when covalently linked to an immunogen enhances the host's immune response to that immunogen regardless of whether the complex of carrier and immunogen is administered parenterally, enterally, or orally to the host. In addition, processes are provided for production of the complexes, as well as hybrid DNA sequences encoding complexes, recombinant DNA molecules bearing the hybrid DNA sequences, transformant hosts and vaccines comprising the complexes as well as methods for production of the vaccine.

16 Claims, 7 Drawing Sheets

OTHER PUBLICATIONS

C. Joyce et al. "Construction of a Plasmid that Over Produces the Large Proteolytic Fragment (Klenow Fragment)of DNA Polymerase 1 of *Escherichia coli*", Proc. Natl. Acad. Sci. USA, 80, (1983), pp. 1830–1834.

J. Mott et al. "Maximizing Gene Expression from Plasmid Vectors Containing the λ $P_L$ Promoter: Strategies for Over Producing Transcription Termination Factors ρ", Proc. Natl. Acad. Sci., USA, 82, (1985) pp. 88–92.

C. Marcahl et al. "Un Systeme de Vecteurs Destine a Permette L'Excretion D'Une Proteine Determinee Par Un Gene Clone", C.R. Acad. Sc. Paris, V. 288, Part D, pp. 275–277 (Jan. 15, 1979).

Freudl et al. "Cell Surface Exposure of the Outer Membrane Protein OmpA of *Eschericha coli* K–12", Chemical Abstracts, vol. 105, No. 1, p. 306, Ref. No. 3151X and J. Mol. Biol. 188(3): pp. 491–494 (1986).

E. Minkley, Jr. "Purification and Characterization of pro–TraTp: The Signal Sequence–Containing Precursor of a Secreted Protein encoded by the F Sex Factor", Chemical Abstracts, vol. 101, No. 3, Jul. 16, 1984, p. 158, Ref. No. 18263b, and J. Bacteriol. 158(2) :464–73 (1984).

A. Chatbit et al. "Probing the Topology of a Bacterial Membrane Protein by Genetic Insertion of a Foreign Epitope: Expression at the Cell Surface", The Embo Journal, vol. 5, No. 11, pp. 3029–3037, IRL Press Ltd., Oxford, UK (Nov. 1986).

Melchers et al. "The Lipoprotein of the Outer Membrane of *Escherichis coli*; A B–lymphocyte Mitogen", The Journal of Experimental Medicine 142:473 (1975).

Bessler et al. "Induction of Lymphocyte Proliferation and Membrane Changes by Lipopeptide Derivatives of the Lipoprotein from the Outer Membrane of *Escherichia coli*", Z. Immun, Forsch 153:11 (1977).

Bessler et al. "Protein I and Protein II from the Outer Membrane of *Escherichia coli* are B–lymphocyte Mitogens", Z. Immun, Forsch 155:387 (1987).

Zollinger et al. "Enhancement of Immunologic Activity by Noncovalent Complexing of Meningococcal Group B Polysaccharide and Outer Membrane Proteins", Seminars in Infectious Diseases, vol. 4, Bacterial Vaccines, (Robbins JB Hill) Chapter 35, p. 254 (1980).

Bessler et al. "The Mitogenic Principle of *Escherichia coli* Lipoprotein: B–Lymphocyte Mitogenicity of the Synthetic Analouge Palmitoyl–Tetrapeptide", Biochemical and Biophysical Research Communications 121:55 (1984).

Jung et al., "Increased Production of Specific Antibodies by Presentation of the Antigen Determinants with Covalently Coupled Lipopeptide Mitogens", Angew. Chem. Int. Ed. Engl. 24, p. 872, (1985).

Bessler et al. "Specific Antibodies Elicited by Antigen Covalently Linked to a Synthetic Adjuvant", Immunobiol. 170, 239, (1985).

Bessler et al. "Synthetic Lipopetide Analogs of Bacterial Lipoprotein are Potent Polyclonal Activators C. for Murine B–Lymphocytes", The Journal of Immunology 135, 1900 (1985).

Vordermeier et al. "A Defined Fragment of Bacterial Protein I (Ompf) as a Polyclonal B–Cell Activator", Infection and Immunity 51, 233 (1986).

Bessler et al. "B–Lymphocyte Mitogenicity In Vitro of a Synthetic Lipopeptide Fragment Derived from Bacterial Lipoprotein", Z. Physiol. Chem Bd. 363 S. pp. 767–770, Jul. 1982.

Johnson et al. "Synthetic Analogues of the N–Terminal Lipid Part of Bacterial Lipoprotein are B–Lymphocytes Mitogens In Vitro and In Vivo", Immunobiol. vol. 165, pp. 27–35 (1983).

Supplement European Search Report.

Wetzler et al. J. Exp. Med. 168: pp. 1883–1897 (1988).

Perumal et al, J. of Biol Chem. 259:5357–5360 1984, "The Product of the F. Sex Factor TraT Surface Exclusion Gene is a Lipoprotein" (Abstract Only).

Palva FEMS Symp. "Regulation of Outer Membrane Proteins" vol. 25, 31–37 1985.

Benz et al Crit. Rev Biochem 19:145–190, 1985 "Porin From Bacterial & Mitochondrial Outer Membranes".

Bessler et al Immunobiol. 170:239–244 1985 "Specific Antibodies Elicited by Antigen Covalently Linked to a Synthetic Adjuvant".

Avrameus et al, Scand J. Immol vol. 8 7:7–23, 1978 Coupling of Enzymes to Antibodies & Antigens.

Staros et al Analytical Biochem 156:220–222 1986. Enhancement of N–Hydroxysulfosuccininido of Water Soluble Carbodiimide Medial Coupling Reactions.

Makela et al Seminars in Infectious Disease vol IV Bacterial Vaccines 1982 pp. 360–365, "Porins: The Major Outer Membrane Proteins of Enteric Bacteria on Protective Antigens".

Hoffman et al Science 237:639–642, 1987.

Brown et al, Vaccine 12:102–108, 1994 Safety, Immunogenicity and United Efficacy Study of a Recombinant Plasmodium Falciparium Circumsponorate Vaccine in Thai Soldiers.

Riley Immunology Today 13:127–130, 1992 See pp. 129–130.

Henning et al. Eur. J. Biochem 136:233–240, 1983.

Jung et al Angew Chem Int Ed Engl. 24:872–873, 1985.

Silhavy et al, J. Cell. Biochem Suppl 7B Abstract 332.

Nagahari et al EMBO J. 4 (13A):3589–3592 1985 (Abstract Only).

Svenson et al, Infection & Immunity 25:863–872, 1979.

Becker et al FEBS Lett. 204:145–150, 1986.

Nickardo et al Biochemical & Biophysical Res. Communications 76:324–330, 1977.

Osborn et al Ann Rev Microbiol 34:369–422, 1980.

Henning et al Eur J. Biochem 136:233–240, 1983.

Barbero et al J. Biotechnol 4 255–268, 1986.

Bessler et al Z. Immun–Forsch 155 387–398, 1979.

Takahara et al J. Biol Chem 260:2670–2674, 1985.

Chang et al Nature 315:151–154, 1985.

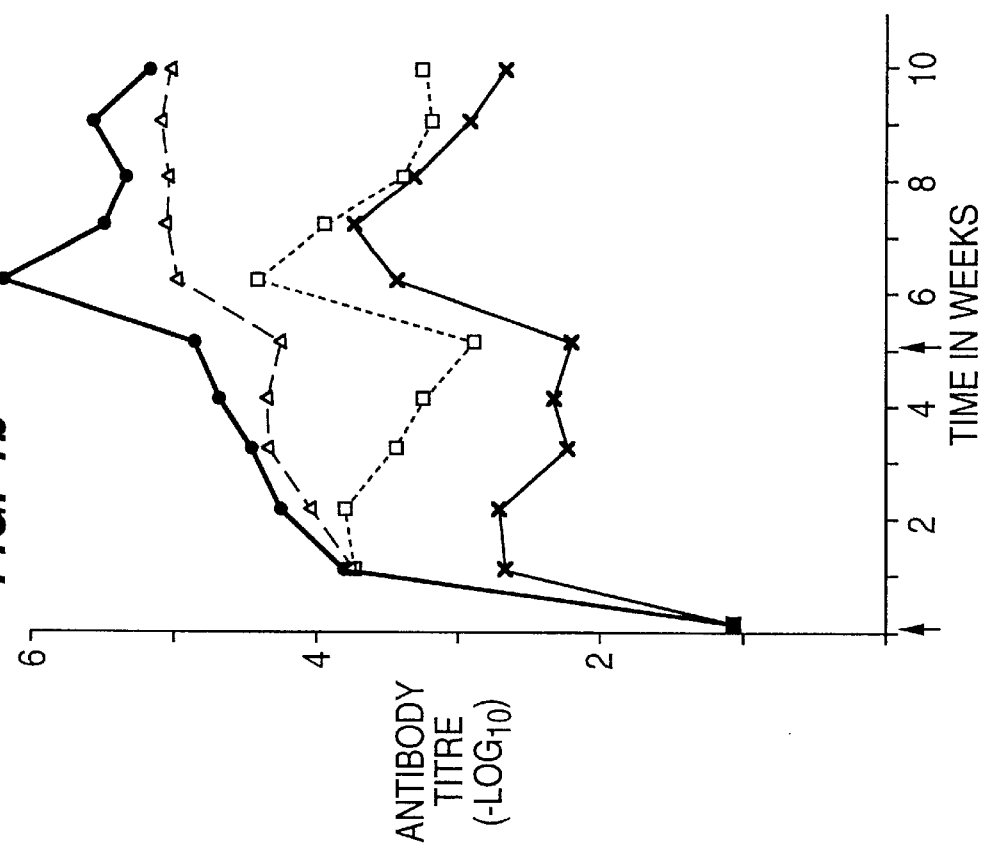
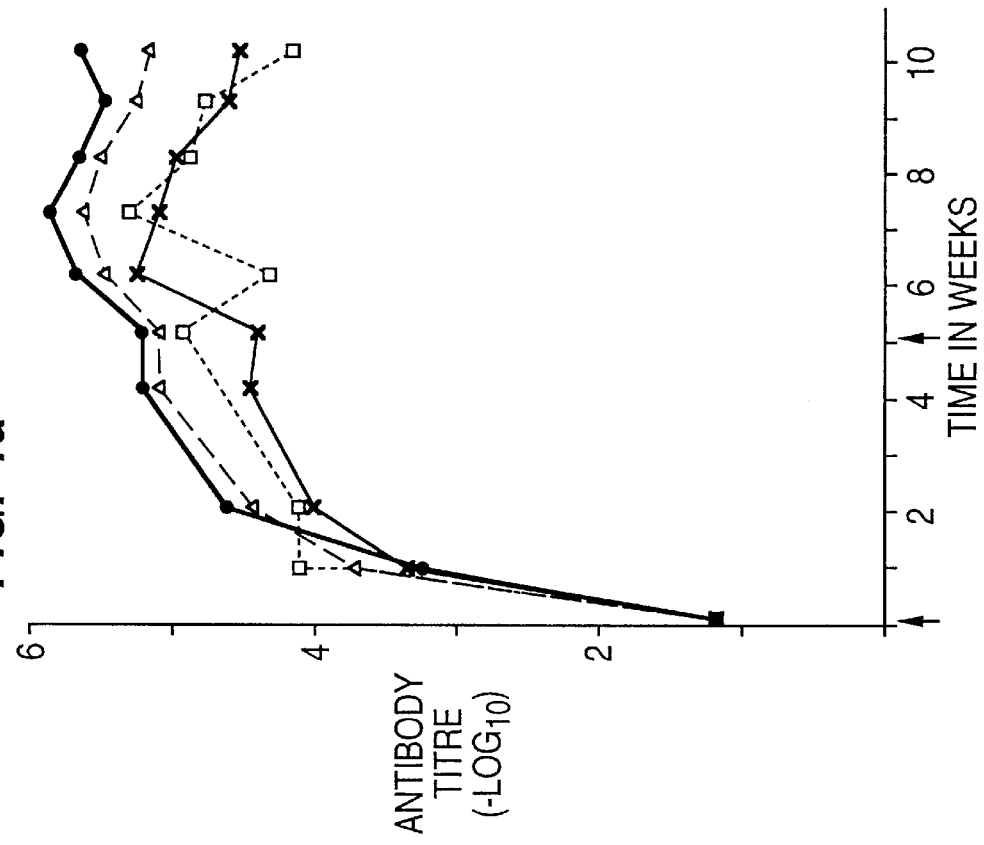

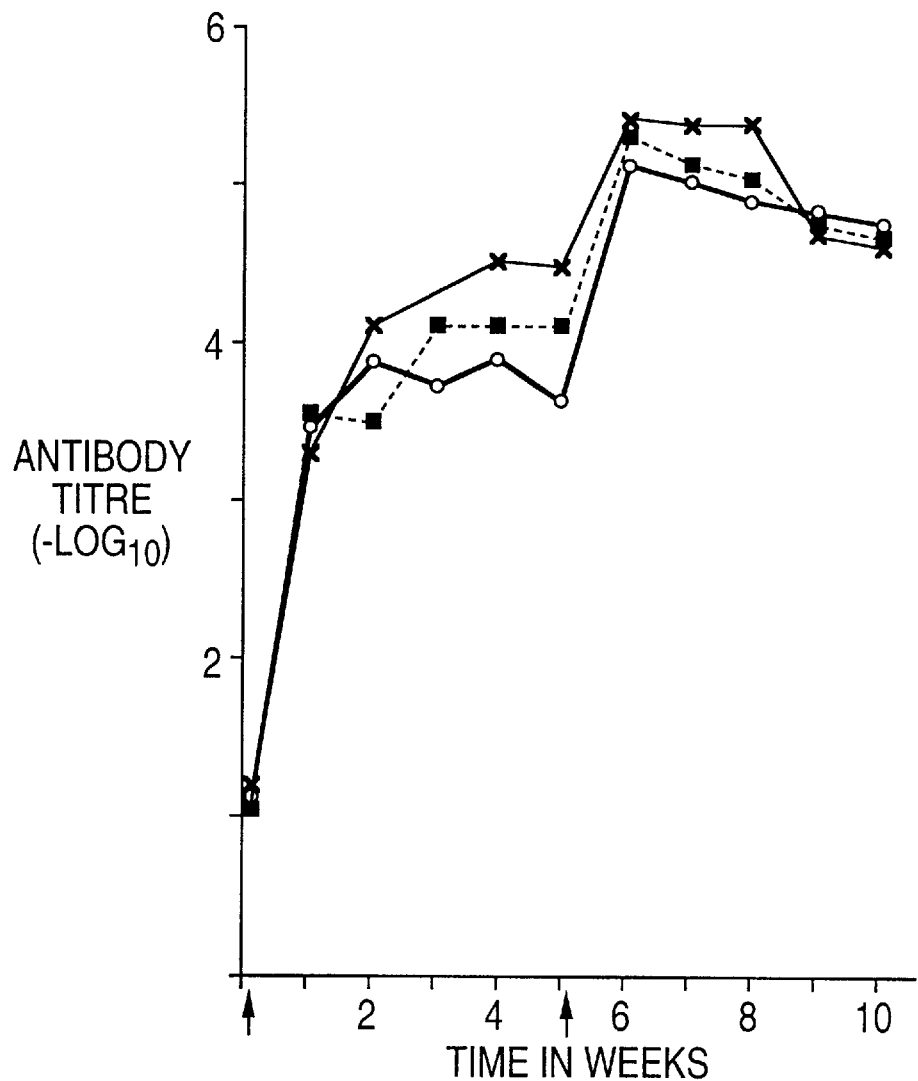

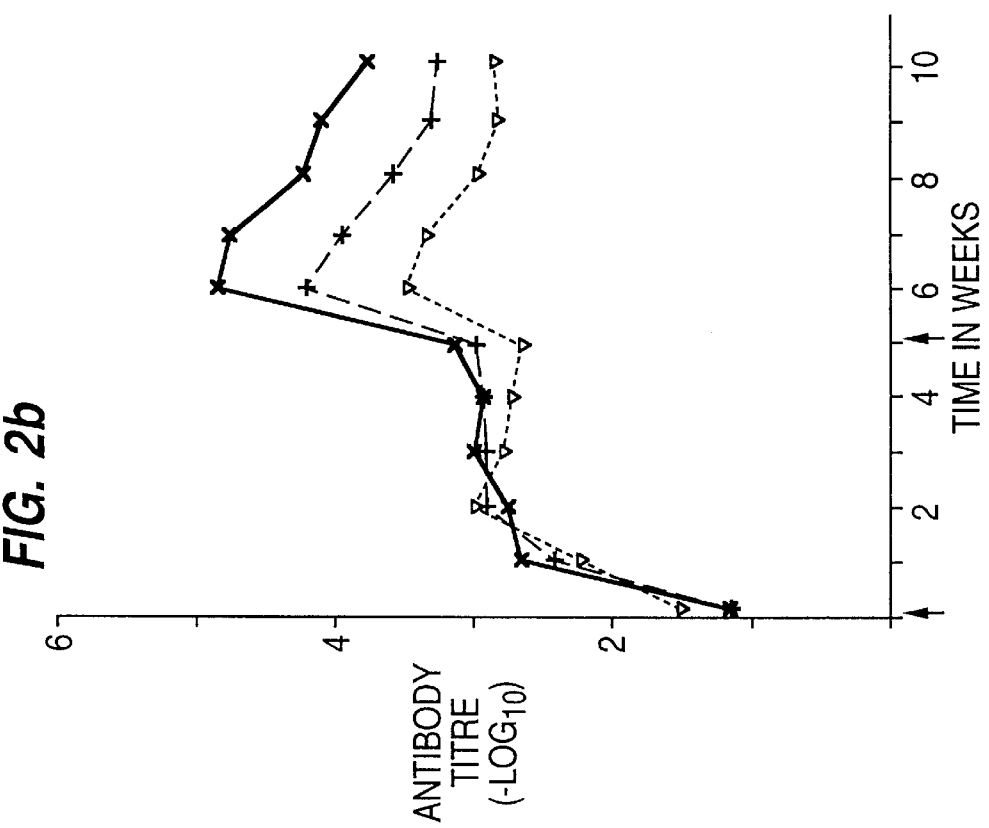
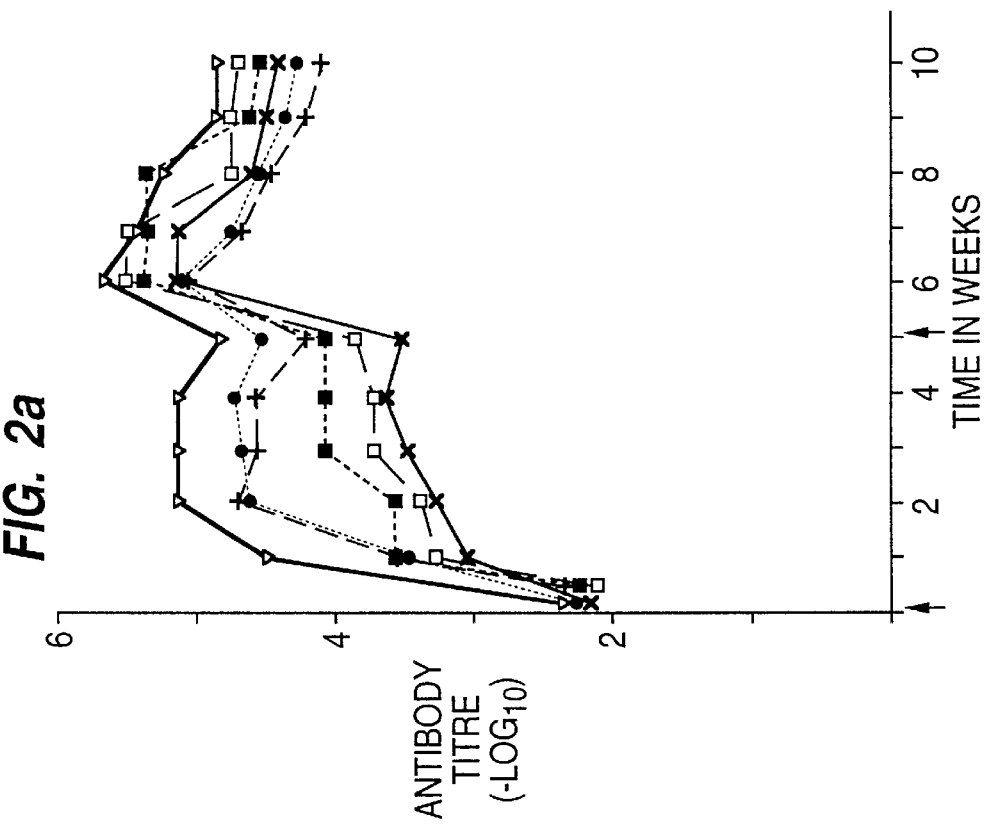

IMMUNOPOTENTIATING COMPLEXES COMPRISING TRAT PROTEINS

This application is a continuation of application of 07/903,121, filed on Jun. 23, 1992, which is a continuation application of 07/159,968, filed Dec. 21, 1987 both abandoned.

TECHNICAL FIELD

The invention relates to a class of molecules which when linked to an immunogen can enhance the host's immune response to that immunogen regardless of whether the complex is administered parenterally, enterally or orally.

DEPOSITION OF STRAINS

Reference to ATCC 67331, is to an *E. coli* strain deposited with the American Type Culture Collection at 12301 Parklawn Drive, Rockville, Md. 20852, USA on 2 Mar., 1987.

BACKGROUND ART

In order to protect an animal against an invading pathogen (bacterial, viral or parasite) it is often advisable to vaccinate the animal with the whole organism or with such subunits of the pathogen as to elicit a protective immune response in the host. The immune response generated to such antigenic challenge can often be augmented by the co-administration of an immunopotentiating agent or adjuvant. The best of these agents are the depot type adjuvants (such as Freund's complete adjuvant, Freund's incomplete adjuvant and montanide). These adjuvants are capable of increasing the antibody response after antigen injection to some 50 to 100 times the level obtained with antigen injected alone.

Whilst adjuvants such as Freund's complete adjuvant, Freund's incomplete adjuvant and Montanide can greatly enhance the immune response to an antigen, they suffer from some disadvantages. When used with an antigen in an injectable form, large lesions often form at the site of injection, a situation which renders them unsatisfactory for such use in humans, pets or in meat animals. Furthermore, these adjuvants fail to act as immunopotentiating agents when administered orally or enterally.

DESCRIPTION OF THE INVENTION

This invention relates to a class of molecules which when linked chemically or genetically to an immunogen or hapten can enhance the host's immune response to the immunogen or hapten regardless of whether the complex is administered parenterally, enterally or orally. In addition their use does not result in the formation of large lesions at injection sites.

Molecules which have this activity can be defined as having the general property of being membrane proteins and the examples described herein are from specific types of membrane proteins, more specifically the outer membrane proteins of Gram negative bacteria. Examples cited specifically include the TraT protein, an outer membrane protein of certain strains of *E. coli* which is responsible for the resistance of these strains to killing by serum. Other proteins of this class are the *E. coli* outer Membrane proteins OmpA and OmpF. When quantities of TraT, OmpA or OmpF (hereafter called carrier) are injected intramuscularly into mice, without adjuvant, an antibody response is elicited which is comparable to that elicited when a soluble protein such as BSA, flagellin or sheep IgG is mixed with Freund's incomplete adjuvant and then injected. In fact, the antibody response elicited by these outer membrane proteins is so high as to be only marginally increased by adjuvation with Freund's incomplete adjuvant.

It has also been found that oral administration of TraT or OmpA results in the stimulation of significant titres of anti-TraT (1/4096) or anti-OmpA (1/892) serum antibodies.

Similarly it has been found that feeding of moderate quantities ($10^9$–$10^{10}$) of Salmonella or *E. coli* containing TraT in the outer membrane also enhances production of anti-TraT antibodies.

Covalent coupling of a hapten (Dinitrophenol, DNP), peptide (CSP) or a protein (Bovine Serum Albumin, BSA) to OmpA or TraT also acts to enhance the immune response to the DNP, CSP or BSA.

In a first embodiment the invention provides a complex comprising an immunogen coupled to a carrier molecule, such that the carrier molecule causes the immune response of a host to the immunogen to be enhanced when the complex is administered to said host, regardless of whether the complex is administered parenterally, enterally or orally, wherein said immunogen comprises either an antigen or a hapten and said carrier molecule comprises an integral membrane protein of prokaryote or eukaryote origin.

In a preferred embodiment the carrier molecule is an outer membrane protein of a Gram negative bacterium.

Preferably said Gram negative bacterium is *E. coli* or a Salmonella species.

More preferably the carrier molecule is the TraT protein or the outer membrane protein OmpA or OmpF, produced by strains of *E. coli*.

Preferred immunogens of the invention include CSP, the viral capsid protein VP7 from a rotavirus strains and all or part of the eukaryotic protein minactivin.

The immunogen-carrier complex may be formed by chemical means including: conjugation, for instance, by using either a suitable conjugating or linking agent; and modification and/or reaction of functional groups present on carrier and/or immunogen.

Thus, the invention provides a process for the production of a complex comprising, an immunogen coupled to a carrier molecule, said carrier molecule being an integral membrane protein (imp), of prokaryote or eukaryote origin and said immunogen comprising either an antigen or a hapten, wherein the carrier molecule causes the immune response of a host to the immunogen to be enhanced when the complex is administered to said host, regardless of whether the complex is administered parenterally, enterally or orally, which process comprises one or more of the following steps:

a) reacting the immunogen with the carrier to form said complex;

b) chemically modifying the immunogen to provide at least one functional group capable of forming a chemical linkage, and reacting the modified immunogen and carrier to form said complex;

c) chemically modifying the carrier to provide at least one functional group capable of forming a chemical linkage and reacting the immunogen and modified carrier to form said complex;

d) chemically modifying the immunogen and the carrier to provide functional groups capable of forming a chemical linkage, and reacting the modified immunogen and modified carrier to form said complex;

e) reacting the immunogen with at least one linking agent and reacting the linked immunogen and the carrier molecule to form said complex;

f) reacting the carrier with at least one linking agent and reacting the immunogen and linked carrier to form said complex;

g) reacting the immunogen and carrier with at least one linking agent and reacting the linked immunogen and linked carrier to form said complex.

A preferred process of the invention comprises:

(i) chemically modifying an immunogen to provide at least one functional group capable of forming a chemical linkage; and (ii) reacting the modified immunogen and the carrier to form said complex.

The linking agent may contain a disulfide bond or be cleavable by acid, base or periodate. Examples of such linking agents include N-(4-azidophenylthio)phthalimide, 4,4'-dithiobisphenylazide, dithiobis-(succinimidyl-propionate), dimethyl-3,3'-dithiobispropionimidate.2HCl, 3,3'-dithiobis-(sulfosuccinimidylpropionate), ethyl-4-aziodophenyl-1, 4-dithiobutyrimidate,HCl, N-succinimidyl-(4-azidophenyl)-1,3'-dithio-proplonate, sulfosuccinimidyl-2-(m-azido-o-nitrobenzamido)-ethyl-1,3'-dithiopropionate, sulfosuccinimidyl-2-(p-azidosalicylamido)-ethyl-1, 3'dithioproplonate, N-succinimidyl-3-(2-pyridyldithio) propionate, sulfosuccinimidyl-(4-azidophenyldithio)-propionate, and 2-iminothiolane. Preferred cross-linking agents are disuccinimidyl tartrate and bis-[2-(succinimidyloxycarbonyloxy)-ethyl]sulfone.

Suitably, linking of the carrier and immunogen may be achieved by coupling the carrier to suitable groups of the immunogen.

Where the immunogen-carrier complex is formed by chemical conjugation, for instance, by using either a suitable conjugating or linking agent, preferred conjugating or linking agents include 1-ethyl-3-(3-dimethyl-aminopropyl) carbodiimide, glutaraldehyde, m-Maleimido benzoic acid n-hydroxysuccinimide ester, or N, $N_1$ Dicychohexyl carbodiimide.

The linkage between the immunogen and the carrier molecule may also be made by the preparation of a hybrid protein molecule, such as is produced by recombinant DNA techniques by the insertion into, or addition to, the DNA sequence coding for the carrier, of DNA coding for the immunogen.

Hence, the invention provides a process for the preparation of said complex of carrier molecule with immunogen, which process comprises preparing a hybrid protein molecule. In a preferred process the hybrid protein molecule is produced by recombinant DNA techniques, by the insertion into, or the addition to, the DNA sequence coding for the carrier, of DNA coding for the immunogen.

The invention also provides a hybrid DNA sequence which consists of: a first DNA sequence comprising a DNA sequence which acts as a coding sequence for at least part of an integral membrane protein of prokaryote or eukaryote origin fused to a DNA sequence coding for the amino acid sequence of an immunogen; or a second DNA sequence which hybridizes to said first DNA sequence, from whatever source obtained, including natural, synthetic and semi-synthetic sources; a DNA sequence related by mutation, including single or multiple base substitutions, deletions, insertions and inversions to said first DNA sequence; or a DNA sequence comprising sequences of codons which, on expression, code for a polypeptide displaying similar immunological or biological activity to a polypeptide coded for on expression of the codons of any of the foregoing hybrid DNA sequences and inserts.

Preferred hybrid DNA sequences of the invention code for at least part of TraT, OmpF or OmpA, linked to a DNA sequence coding for the amino acid sequence of an immunogen such that the resulting TraT-(OmpF or OmpA) hybrid proteins are exported to and exposed on the host cell surface.

The invention also provides a fused gene comprising a hybrid DNA sequence of the invention fused to a portable promoter. A preferred promoter according to the invention, is the $P_L$ promoter of the bacteriophage lambda.

Further, the invention provides, a recombinant DNA molecule which comprises a hybrid DNA sequence according to the invention and vector DNA, wherein the vector DNA is plasmid, bacteriophage, viral or cosmid DNA.

A preferred recombinant DNA molecule of the invention includes an expression control sequence operatively linked to the hybrid DNA sequence.

Particularly preferred recombinant DNA molecules according to the invention Include: pBTA371, pBTA439, pBTA449, pBTA450 and pBTA586.

Within the scope of the invention is a process for the manufacture of a recombinant DNA molecule which process comprises:

introducing into a cloning vehicle, a hybrid DNA sequence according to the invention.

Preferably the process also includes the step of introducing an expression control sequence into the cloning vehicle.

The invention also provides a host transformed with at least one recombinant DNA molecule according to the invention.

Suitable hosts include *E. coli* and *Salmonella sp.*

A preferred transformant is ATCC 67331 (also designated CCTCC 87026).

Also included within the scope of the invention is a process for transforming a host, which process comprises the step of: introducing into a host a recombinant DNA molecule according to the invention.

In a further embodiment the invention provides the complex of carrier with immunogen adapted for parenteral injection into a host or adapted for oral or enteral administration, to elicit both a humoral and mucosal antibody response.

Included within the scope of the invention is a process for the preparation of the complex of carrier with immunogen in a form adapted for parenteral, enteral or oral administration to a host which process comprises preparing the complex and.adding it to a pharmaceutically acceptable diluent.

Preferably the invention provides a whole bacterial cell vaccine comprising a hybrid protein according to the invention is exposed on the bacterial cell surface for presentation to the immune system. The whole cell vaccine may be a live or killed whole cell oral vaccine. Alternatively the hybrid protein can be purified from the cell membrane or cellular contents and used as a subunit vaccine administered parenterally, enterally or orally.

The invention also provides a process for the manufacture of a microorganism with the genetic information for the biosynthesis of a hybrid protein comprising at least an immunogen and a carrier comprising at least part of an imp of prokaryote or eukaryote origin, such that the resulting hybrid peptide is exposed on the host cell surface which process comprises culturing a microorganism carrying the necessary genetic information. Where the microorganism is used to provide a subunit vaccine, the process additionally comprises purifying the hybrid peptide from the cell membrane or cellular contents.

Figure 2D:
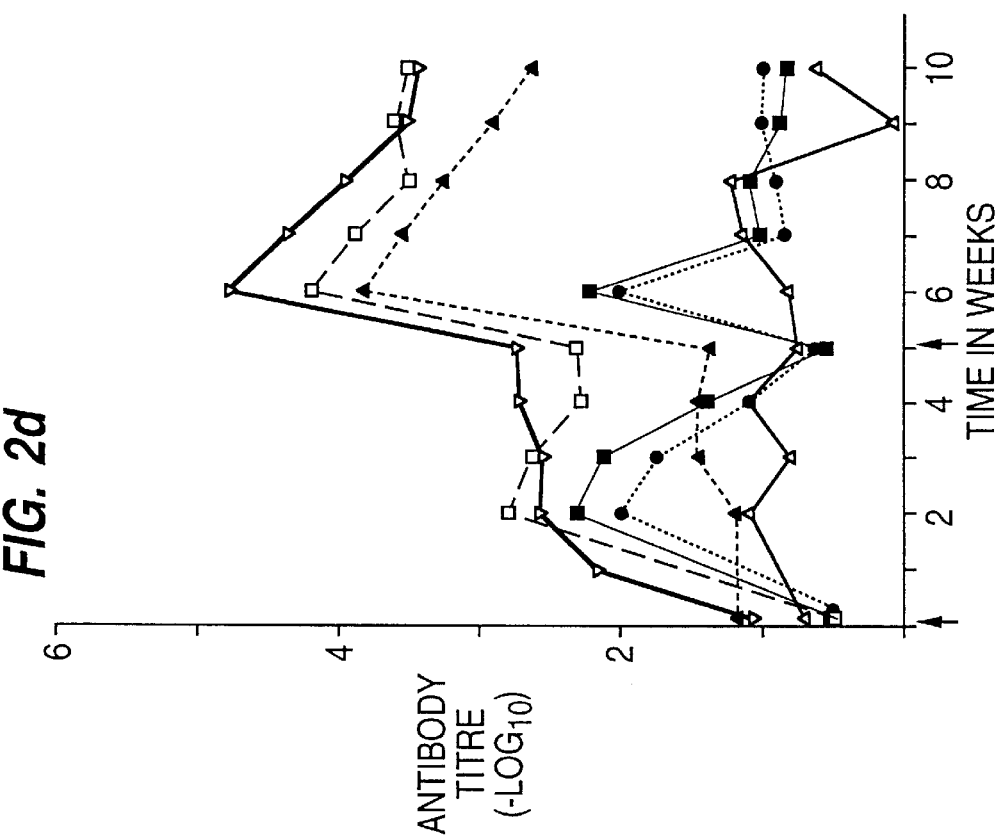
FIG. 2 Stimulation of the antibody response to DNP and BSA by coupling to TraT and OmpA.
Figure 2C:
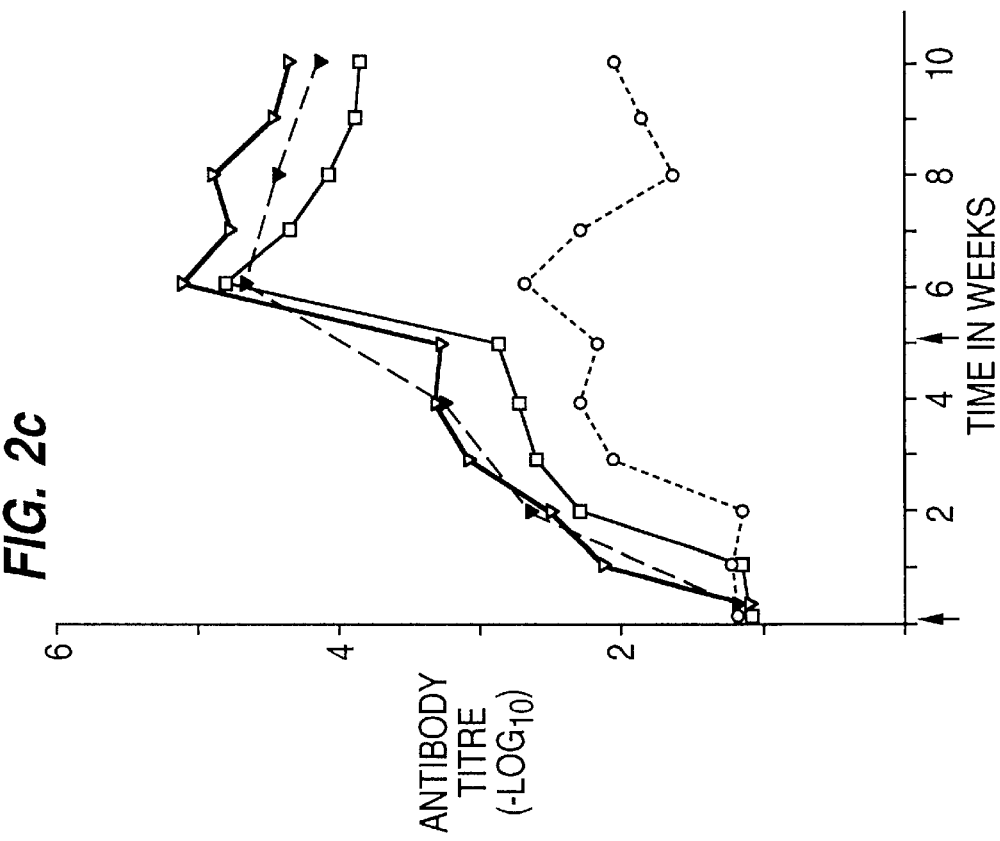

Dinitrophenylated preparations of TraT (+——+) Omp A (X——X) and BSA (▼——▼) were compared for their ability to stimulate anti-carrier (FIG. 2a) and anti-DNP antibody responses (FIG. 2b) following im injection. The antibody response to TraT (●——●) and Omp A (■——■) injected alone was also determined. Similarly BSA was injected in saline (O——O), mixed in FIA (▼——▼) or covalently conjugated to TraT (▽——▽) or Omp A (□——□) and the anti-BSA response was determined (FIG. 2c). The anti-TraT and anti-Omp A responses to these congugates are shown in FIG. 2a. The immunopotentiating activity of imps was examined when BSA was injected covalently linked to TraT (▽——▽) or Omp A (□——□), when it was mixed with TraT (▲——▲) or Omp A (■——■) or when it was injected at a separate site from TraT (Δ——Δ) or Omp A (●——●) (FIG. 2d).

Figures 1, 3A:
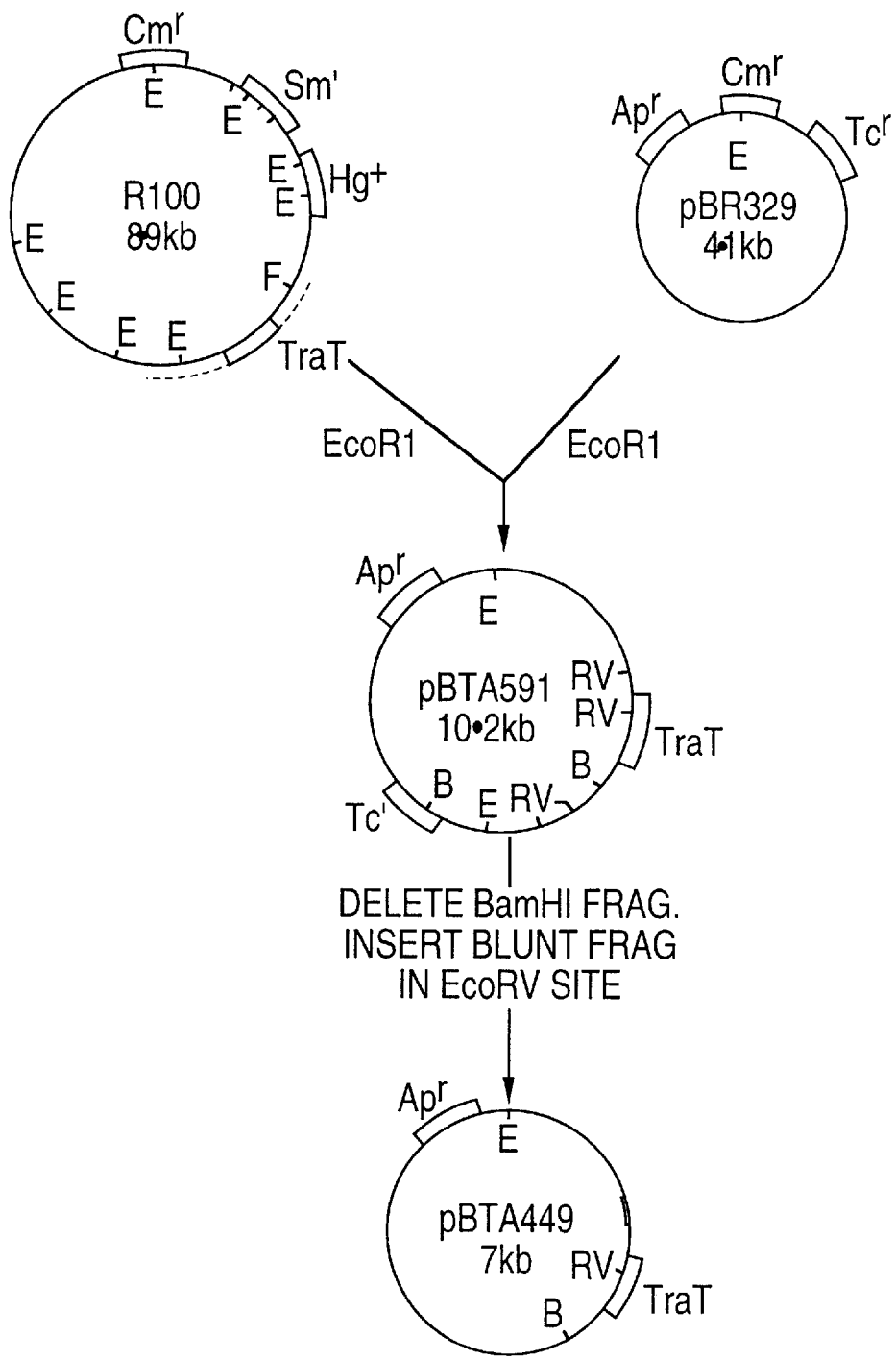
FIG. 1 Modifications of the immune response by adjuvants. Rabbits were injected i.m. with TraT, (FIG. 1a) and BSA (FIG. 1b) alone or in combination with various adjuvants. TraT and BSA were mixed with F.I.A. (Δ-Δ); Montanide 888 (●-●), Alhydrogel (□-□); saline (x-x) FIGS. 1a+1b. A comparison of the antibody response generated to TraT (x-x) OmpA (■-■) and OmpF (o-o) injected in saline is presented in FIG. 1c.

FIG. 3a shows the construction of the plasmids and pBTA449, pBTA439 and pBTA371.

Figure 4A:
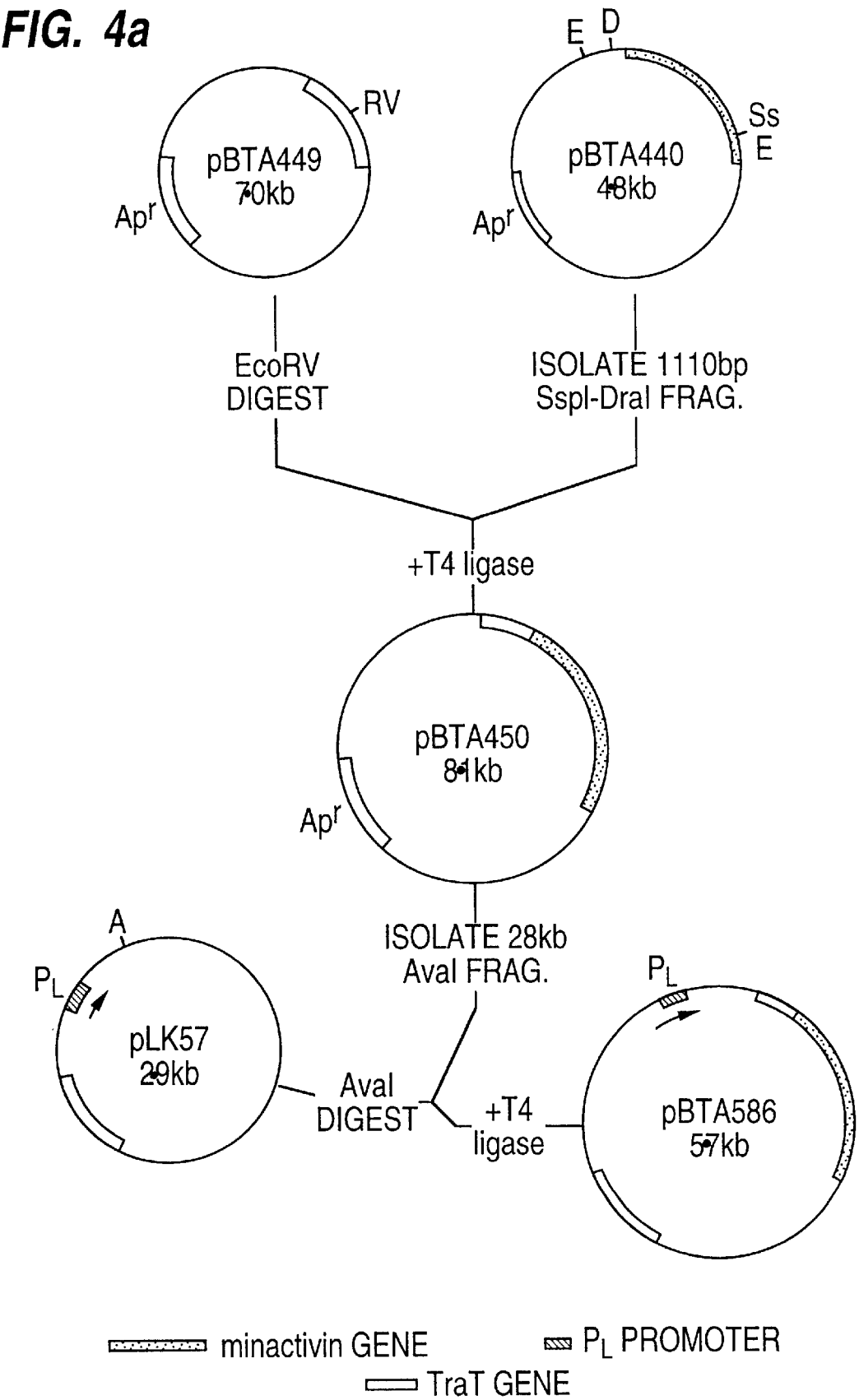

FIG. 4a shiws the construction of the plasmids pBTA450 also pBTA586.

Figures 2, 3A:
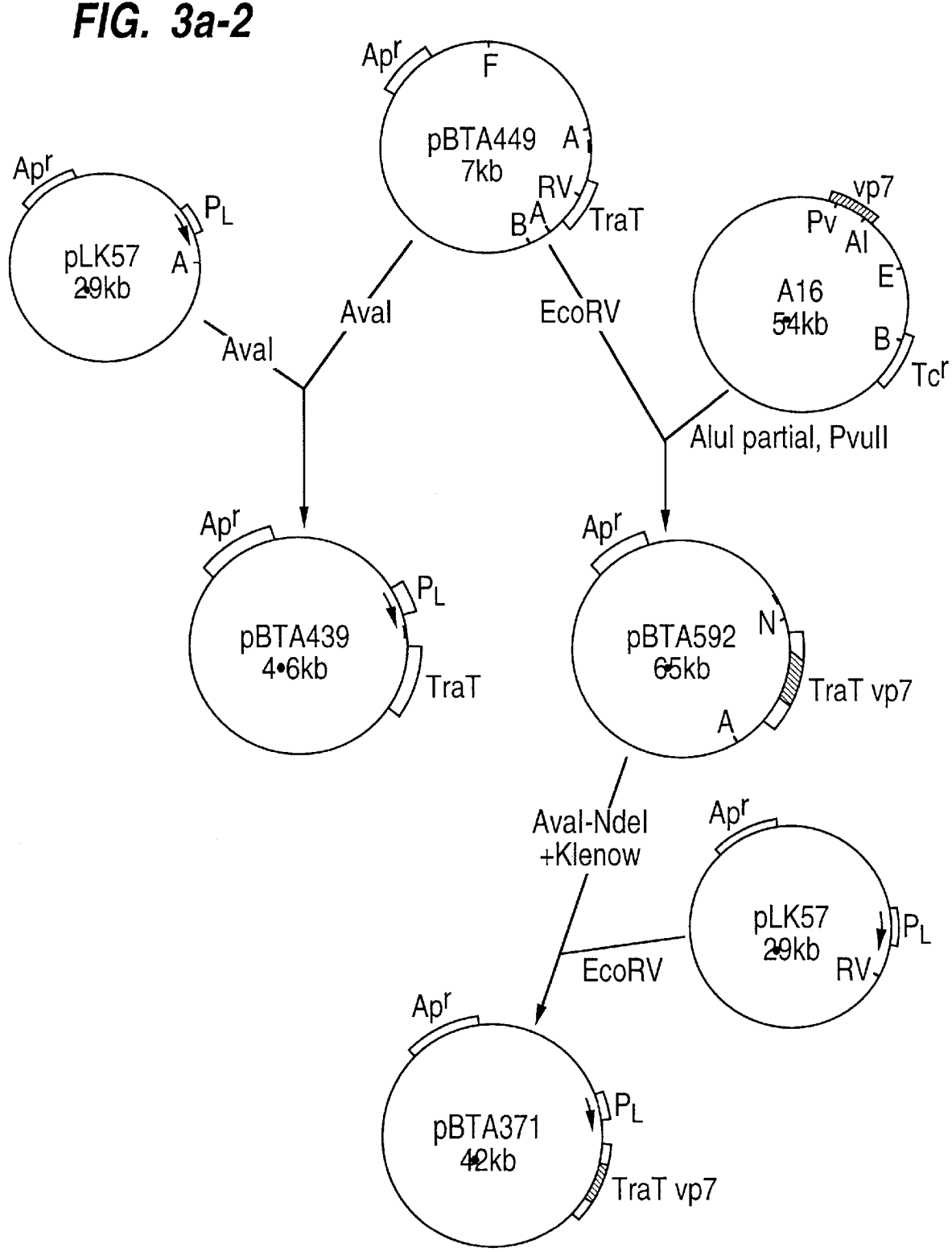

Abbreviations (FIG. 3 and 4): Resistance to; ampicillin, $Ap^r$; chloramphenicol, $Cm^r$; mercuric chloride, $Hg^+$; tetracycline, Tc; VP7 structural gene, VP7; TraT structural gene, TraT,; TraT VP7 gene fusion, TraT-VP7; lambda bacteriophage $P_L$ promoter region, $P_L$. Restriction endonucleases, Al, AluI; A, AvaI; D, DraI B, BamHI; E, EcoRI; N, NdeI; Pv, PvuII; RV, EcoRV; Ss Sspl.

BEST MODE OF CARRYING OUT THE INVENTION

The following examples illustrate preferred embodiments of the present invention, and are in no way limiting on the scope of the invention.

EXAMPLE 1

Isolation of TraT, OmpA and OmpF

E.coli (Strain BTA 1352 containing the plasmid pBTA439) were grown in a fermenter at 30° C. in MEB medium. Cells were harvested following 2 hours of heat induction of TraT at 42° C. Bacteria were concentrated to 2 litres using a 0.1μ hollow fibre cartridge in a Amicon DCIOLA concentrator. The cells were then washed with 10 liters of distilled water and reconcentrated to 800 ml. The bacterial slurry was then removed from the concentrate and the outer membrane proteins (TraT, OmpA and OmpF) extracted from the cells by the addition of 200 ml of 1M sodium acetate buffer pH 2.5, followed by 1 liter of 10% cetrimide (Sigma) in 40% ETOH plus 1M Ca $Cl_2$. The extraction was allowed to proceed overnight at room temperature, (RT) after which the bacteria were removed by centrifugation (17,000×g, 20 min).

TraT and OmpF were precipitated from the supernatant by the addition of ethanol to 50% and centrifugation (40000×g, 10 min). OmpA was then precipitated from the final supernatant by addition of ethanol to 80%.

Ion Exchange Chromatography

The 50% ethanol pellet containing OmpF and TraT was resuspended in 20 mM Na acetate buffer pH5.0 containing 0.5% Zwittergent, and loaded onto a 5×50 cm colunmf DEAE Sepharose (Pharmacia Fine Chemicals) previously equilibrated with 20 mM Na Acetate buffer pH 5.0 containing 0.1% Zwittergent. TraT was found in the column flow through, and bound OmpF was eluted from the column using a linear gradient of 0–1.0M NaCl in equilibration buffer. Fractions were analysed by SDS-PAGE using a modification of the method of Laemmli (Laemmli, U.K. NATURE (LOND) 227:680 1970; Salit et al., *J.Exp. Med.* 151:716. 1980) and fractions containing isolated TraT or OmpF were pooled and concentrated by ethanol precipitation.

Sephacryl S-300 chromatography

The 80% ethanol pellet containing OmpA was resuspended in 1% SDS in 20 mM Tris. HCl.pH 8.8. Fractions were collected, analysed by SDS-PAGE and fractions containing OmpA were pooled and concentrated by ethanol precipitation.

Proteins purified by the above methods were found to be free of LPS when examined by SDS-PAGE and silver stained by the method of Tsai C. M. and Frasch, C. E. Anal. Biochem 119:115. (1982).

Dinitrophenylation of Carriers

TraT, OmpA and OmpF were dintrophenylated according to the method of Little and Eisen "Methods in Immunology and Immunochemistry" (E. D. Williams, CA and Chase, M. H.) 1, p.128 Academic Press, N.Y. (1967). Briefly, carriers (in 0.1M carb/bicarb buffer pH 9.5) were reacted with a 0.1M solution of DNFB (in Acetone) overnight at RT. The proteins were then dialysed extensively against the coupling buffer.

Glutaraldehyde coupling

Bovine serum albumin (BSA) (from Sigma Chemical Co. St. Louis, Mo.) was coupled to TraT, OmpA and OmpF using the two step glutaraldehyde procedure of Avrameus et al (1978). Briefly, BSA was reacted with 0.2% glutaraldehyde for 2 hrs at R.T. The protein was then dialysed overnight against carb/bicarb buffer pH 9.5 followed by the addition of omp's at a molar ratio's of 1:1 BSA:omp and reacted for 24 hrs at RT. Finally ethanolamine (Sigma) was added to a final concentration of 0.1M, (1 hr, RT) followed by overnight dialysis at 4C against 0.1M carb/bicarb buffer pH 9.5.

ANTIGEN ADMINISTRATION

1. Rabbits

New Zealand white rabbits (2–2.5 kg) were injected intramuscularly with antigen in 0.5 ml of sterile physiological saline.

Injections were performed on days 0 and 36. Weekly bleedings were obtained from the longitudinal vein in the rabbits ear and antibody titres were measured by a standard ELISA using TraT, OmpA, BSA or DNP-sheep IgG as coating antigens.

2. Mice

Female C57BL/6J mice (18–22 gm) were obtained from the Animal Resources Centre (Perth, Western Australia). All mice were starved for 3–4 hours prior to oral or intramuscular (i.m.) administration of antigens. Mice were fed antigen at appropriate concentrations in 0.5 ml of 0.1M carb/bicarbonate buffer pH9.5 using a specially prepared feeding needle. Parallel doses of antigen were injected i.m., in 0.1 ml of sterile physiological saline, into the left hind leg. Groups of 5 mice receiving antigen either orally or im were given two identical doses of antigen, on day 0 and day 14. A blood sample was taken (approx. 0.5 ml) from the retro-orbital plexus on day 14 and day 21. Mice were then sacrificed by cervical dislocation and gut washes performed on the small intestine in the following manner. The small intestine was carefully removed and a small quantity of washing buffer (1.0 ml, 30 mM Tris.HCl pH8.8, 0.9% NaCl, 50 mM EDTA plus 1.0% Tween 20) introduced into the lumen of the gut via a blunt ended feeding needle. After gently kneading the intestine and contents were squeezed out through forefinger and thumb. Gut washes so obtained were immediately centrifuged to remove debris and stored at −20° C. until assayed. Blood samples were allowed to clot at 4° C. before removal of the serum and storage at −20° C.

Enzyme Linked Immunosorbent Assay (ELISA)

The ELISA for the determination of antibody titres was perfomed as described previously by Russell-Jones et al. J. Exp. Med 160:1467, (1984). Titres are expressed as the reciprocal of the antiserum dilution, which gave a ELISA reading of 0.5 after 45 mins at 37° C.

EXAMPLE 2

Effect of adjuvant on the antibody response to integral membrane proteins

The potential of imps to act as self adjuvanting molecules when injected i.m. was examined. The antibody titre generated when TraT FIG. (1a, x-x) or BSA FIG. (1b x-x) were injected alone was compared to that generated when TraT (FIG. 1a) or BSA (FIG. 1b) were mixed with a number of adjuvants.

Intramuscular administration of TraT, in saline quickly elicited high titres of serum antibody to the immunizing agent (FIG. 1a). In fact the titres generated by TraT in saline could only be increased by a factor of 4–8 fold by injection of this antigen in adjuvants such as montanide or FIA (FIG. 1a). This is in direct contrast to the response generated by the soluble antigen BSA. In this case a poor antibody response was generated to the antigens.administered in saline, but was markedly increased 60–100 fold by injection of the antigen in FIA or montanide (FIG. 1b).

Similarly injection of OmpA and OmpF in saline alone also elicited high serum Ab titres. In fact, surprisingly similar antibody titres were elicited by injection of 100 μg TraT, OmpA or OmpF (FIG. 1c).

EXAMPLE 3

Examination of the adjuvanting ability of immunogen—imp complexes

TraT and OmpA were examined for their ability to augment anti-hapten (DNP) and anti-protein (BSA) responses. The two imps were substituted with DNP using dinitrofluorobenzene (see Example 1) or were glutaraldehyde cross-linked to BSA (see Example 1) and then injected i.m.

Coupling of DNP or BSA to either TraT or OmpA had little effect on the generation of an anti-imp response (FIG. 2a, cf 1c). Dinitrophenylation of the imps did however increase the anti-DNP response some four to sixteen fold higher than the response seen to DNP-BSA when it was injected in saline (FIG. 2b). Similarly the anti-BSA response was greatly enhanced when BSA was administered in FIA (FIG. 2c). The immunopotentiating effect of TraT or OmpA on the anti-BSA response was greatest when BSA was covalently linked to the imps. In fact injection of BSA at a separate site from the imp actually depressed the secondary response to BSA (cf 2d and 2c).

EXAMPLE 4

Effect of Dose on the immune response to TraT

The effect of increasing dose of TraT administered either i.m. or per os. was examined in mice.

Groups of 5 mice were immunized by intramuscular injection or oral feeding with increasing doses of TraT. Mice received doses on day 0 and day 14. On day 21 mice were bled, sacrificed and gut washes obtained. Antibody titres were increased by ELISA.

As can be seen from Table 1 increasing doses of TraT administered orally or parenterally led to a dose dependent increase in serum anti-TraT Ab response.

Parenteral administration was however much more effective than oral administration.

TABLE 1

| Dose of antigen | Route of administration | | | |
|---|---|---|---|---|
| | intramuscular serum IgG | per os serum IgG | Gut IgA | Gut IgA |
| 0.1 | 2,048 ± 900 | — | 6 ± 2 | 7 ± 4 |
| 1 | 3,565 ± 1,300 | 7 ± 2.6 | 9 ± 3 | 6 ± 2 |
| 2 | 10,809 ± 1,900 | 2 ± 2 | 13 ± 5 | 56 ± 8 |
| 5 | 5,405 ± 400 | 13.9 ± 9 | 24 ± 3 | 42 ± 7 |
| 10 | 28,526 ± 7,280 | 12.0 ± 2 | 16 ± 4 | 18 ± 5 |
| 25 | 24,833 ± 6,040 | 9.1 ± 3 | 6 ± 2 | 7 ± 4 |
| 50 | 49,667 ± 13,020 | 97 ± 25 | 9 ± 5 | 11 ± 6 |
| 100 | 65,536 ± 16,000 | 64 ± 36 | — | — |
| 200 | 150,562 ± 64,000 | 675 ± 400 | 32 ± 20 | 14 ± 7 |
| 400 | 86,475 ± 19,000 | 97 ± 45 | 6 ± 2 | 24 ± 13 |

EXAMPLE 5

Examination of the hapten density on the ability of the imps to act as carriers for an anti-DNP response TraT, OmpA and OmpF were substituted with different ratios of DNP:imp as described in Example 1. Groups of 5 mice were injected i.m with 50 μg doses of the DNP:carrier complex on days 0 and 14. On day 21 mice were bled and the Ab titres determined by ELISA.

Increasing the substitution ratio of DNP to carrier from 0.5:1 to 4:1 increased the anti-hapten response considerably. Substitutions of greater than 10:1 appeared to decrease the anti-hapten response.

TABLE 2

| Antigen | Substitution | Route | Antibody response (serum IgG) |
|---|---|---|---|
| DNP TraT | 0.5:1 | i.m | 21 ± 13 |
| | 1:1 | i.m | 337 ± 71 |
| | 2:1 | i.m | 1552 ± 536 |
| | 4:1 | i.m | 3104 ± 954 |
| DNP - ompA | 0.5:1 | i.m | — |
| | 1:1 | i.m | 84 ± 20 |
| | 2:1 | i.m | 256 ± 109 |
| | 4:1 | i.m | 776 ± 164 |
| DNP - ompF | 0.5:1 | i.m | 7 ± 4 |
| | 1:1 | i.m | 49 ± 12 |
| | 2:1 | i.m | 97 ± 28 |
| | 4:1 | i.m | 337 ± 115 |

EXAMPLE 6

Generation of an anti-CSP response by coupling to TraT

A synthetic peptide derived from the circumsporozoite protein (CSP) antigen of P. faciparum of the following sequence: $NH_2$ Cys (Asn Pro Asn Ala)$_4$, was sythesized and used to conjugate to TraT in order to examine the adjuvating effect of TraT for the peptide antigen.

The CSP antigen was coupled to Tra T using either glutaraldehyde or Maleimidobenzoic acid n-hydroxy succinimide ester (MBS). Conjugates prepare in this way were injected into a) rabbits on day 0, day 28, which were then bled on day 38, or b) groups of 5 mice on day 0 and 14. Mice were then bled on day 21. Antibody titres were determined as described previously.

Immunization of rabbits or mice with the CSP antigen coupled to TraT using either glutaraldehyde or MBS, resulted in the stimulation of an anti-CSP response which was comparable to that seen when the antigen was coupled to BSA and injected in montanide.

TABLE 3

| Antigen (serum) | Coupling procedure | Animal | Dose ($\mu$g) | Antibody anti TraT | Response anti CSP |
|---|---|---|---|---|---|
| CSP-TraT | glutaraldehyde | rabbit | 200 | 28,526 | 147 |
| CSP-TraT | MBS | rabbit | 200 | 12,417 | 1,024 |
| CSP + montanide | — | rabbit | 200 | 28 | — |
| CSP-BSA + montanide | glutaraldehyde | rabbit | 200 | — | 2,353 |
| CSP-TraT | glutaraldehyde | mouse | 50 | 228,209 | 32 |
| CSP-TraT | MBS | mouse | 50 | 3,566 | 128 |
| CSP + montanide | — | mouse | 50 | — | — |
| CSP-BSA + montanide | glutaraldehyde | mouse | 50 | — | 9 |

EXAMPLE 7

Genetic construction of a TraT-immunogen protein complex.

The gene coding for the TraT protein is located on the R plasmid R100 (or R6-5) and the nucleotide sequence of this gene has been determined (Ogata et al, J. Bacteriol 151: 819–827). TraT is an oligomeric lipoprotein situated in the outer membrane which is simultaneously exposed at the cell surface and associated with peptidoglycan, an internal structure. Using these facts a plasmid vector was constructed (FIG. 3a) by initially cloning a 6.0 kb EcoRI fragment of the R100 plasmid which contains TraT into the multicopy plasmid pBR329. Further deletion of an unwanted 3 kb BamHI fragment and inactivation, by insertion of a small blunted ended HaeIII fragment of M13mp8, in an EcoRV site produced pBTA449. This vector plasmid contains the natural TraT promoter which directs the synthesis of TraT. The expression of TraT (or TraT-hybrid proteins subsequently constructed) can be boosted by the replacement of the weak TraT natural promoter with the strong lambda bacteriophage $P_L$ promoter (e.g. in plasmid pBTA439 FIG. 3a or pBTA586 FIG. 4a). The TraT gene contains an EcoRV site (unique to pBTA449) where foreign DNA sequences may be inserted such that fusions between TraT and the encoded foreign protein are exported correctly to the cell surface and result in exposure of the foreign protein segment at the cell surface.

In one example the gene for a viral capsid protein (VP7) was used to form TraT-VP7 hybrid proteins. VP7-is a structural protein of rotavirus and antibodies raised against purified VP7 protein effectively neutralize viral infectivity in cell culture (Dyall-Smith etal 1985 In Infectious Diarrhoea in the young ed. S.Tzipori). Thus the VP7 protein, in an appropriately expressed form, is a prime candidate for inclusion in a rotavirus vaccine.

An AluI PvuII restriction fragment of the rotavirus NCDV VP7 gene was cloned into the EcoRV site of plasmid pBTA449 and subsequently overexpressed with the $P_L$ promoter (pBTA371, FIG. 3a). For expression the plasmid pBTA371 was used to transform E. coli K-12 strain N4830 (Joyce etal, PNAS 80, 1830–1834 1983) which contains the thermolabile cI repressor of Lambda. Cells transformed with pBTA371 were grown overnight in MEB medium (Mott et al PNAS 82, 88–92 1985) with 100 $\mu$g/ml ampicillin at 30° C. Cells were diluted in MEB medium, grown at 30° C. to an $OD_{600}$ of 1.0 when prewarmed (65°) MEB medium was added in equal volume to equilibrate the temperature to 42° C. Following 4 hours of growth at 42° C. the cells were harvested and examined for induction of the TraT-VP7 hybrid protein. In E. coli N4830 high level expression of the TraT-VP7 protein complex (10–15% total cell protein or greater than 500,000 copies per cell) was observed. A significant proportion of this complex was present in the outer membrane fraction.

In another example a method of producing a protein that is a hybrid of part of the TraT protein coding sequence and all or part of a eukaryotic protein coding sequence, minactivin, follows.

As shown in FIG. 4a the plasmid pBTA440 was digested with SspI and DraI and a 1110bp fragment was isolated from an agarose gel. This fragment was ligated to the vector pBTA449 digested with EcoRV creating pBTA450. pBTA450 was then digested with AvaI and a purified 2800 bp fragment ligated to the plasmid pLK57 digested with AvaI to create plasmid pBTA586. This places part of the minactivin coding sequence under the control of the lambda $P_L$ promoter and fused to the coding sequence of the first 80 amino acids of TraT gene, the first 20 of which constitutes a signal sequence that results in the hybrid appearing in the outer membrane of E. coli. This signal sequence is cleaved off during transport to the outer membrane, which is the normal location of the TraT protein.

When plasmid pBTA586 is transformed into an appropriate host, such as N4830, and induced with temperature shift as described above, the TraT-minactivin hybrid protein appears in the outer membrance fraction.

EXAMPLE 8

Oral feeding of strains expressing TraT in the outer membrane

Female C57B1/65 mice (20–25 g) were fed $10^9$–$10^{10}$ bacteria (E. coli or a galE$^-$ mutant of S. typhimurium) expressing TraT in their outer membranes. Controls received the same strains without the TraT protein. After 1 week mice were bled and the anti-TraT titres measured as outlined previously.

Results are expressed in Table 4 as reciprocal antibody titre and represent the average of 10 mice.

TABLE 4

| Antibody Response to Orally Administered Whole Bacteria | | | | | |
|---|---|---|---|---|---|
| | | Anti TraT | | Anti OmpA | |
| Strain | TraT | Serum | Intestine | Serum | Intestine |
| E. coli | − | 3 | 5.2 | 14 | 2 |
| | + | 350 | 15 | 110 | 2 |
| Salmonella | − | 12 | 2 | ND | ND |
| | + | 650 | 6 | ND | ND |

INDUSTRIAL APPLICATION

The current invention is of use in the preparation of vaccines for use in humans, pets and meat animals, and in general for potentiating the response to an antigen on oral, enteral or parenteral administration.

We claim:

1. A substantially pure complex comprising: an immunogen selected from the group consisting of an antigen and a hapten covalently coupled to a carrier molecule which functions as an adjuvant when covalently attached to the immunogen, wherein the carrier molecule comprises a TraT protein, and wherein the carrier molecule causes enhancement of the immune response of a host to the immunogen when the complex is administered to the host, regardless of whether the complex is administered parenterally, enterally or orally.

2. The substantially pure complex according to claim 1, wherein said immunogen is selected from the group consisting of CSP, CSP synthetic peptide NH$_2$ Cys (Asn Pro Asn Ala)$_4$, the viral capsid protein VP7 from a rotavirus, and the protein minactivin.

3. The substantially pure complex according to claim 1 wherein the coupling of the carrier molecule to the immunogen is by chemical means.

4. The substantially pure complex according to claim 3 wherein the coupling is by chemical conjugation comprising use of either a conjugating or a linking agent.

5. The substantially pure complex according to claim 4 wherein the conjugating or linking agent is selected from the group consisting of 1-ethyl-3-(3-dimethyl-aminopropyl) carbodimide, glutaraldehyde, m-Maleimido benzoic acid n-hydroxysuccinimide ester, and N, N$_1$ dicyclohexyl carbodiimide.

6. The substantially pure complex according to claim 4 wherein the linking agent contains a disulfide bond or is cleavable by acid, base or periodate.

7. The substantially pure complex according to claim 6 wherein the linking agent is selected from the group consisting of: N-(4-azidophenylthio)phthalimide; 4,4'-dithiobisphenylazide; dithiobis-(succinimidylpropionate); dimethyl-3,3'-dithiobispropionimidate, 2HCl; 3,3'-dithiobis-(sulfosuccinimidylpropionate); ethyl-4-azidophenyl-1-,4-dithiobutyrimidate, HCl; N-succinimidyl-(4-azidophenyl)-1,-3'-dithiopropionate; sulfosuccinimidyl-2-(m-azido-o-nitrobenzamido)-ethyl-1,-3'-dithiopropionate; sulfosuccinimidyl-2-(p-azidosalicylamido)-ethyl-l,-3'-dithiopropionate;N-succinimidyl-3-(2-pyridyldithio) propionate; sulfosuccinimidyl-(4-azidophenyldithio)-propionate; 2-iminothiolane; disuccinimidyl tartrate; and bis-[2-(succinimidyloxycarbonyloxy)-ethyl]-sulfone.

8. The substantially pure complex according to claim 1 wherein the coupling is by means of genetic linkage, and the immunogen is selected from the group consisting of a protein antigen and a protein hapten.

9. The substantially pure complex according to claim 8 wherein the complex comprises a hybrid protein molecule.

10. The substantially pure complex according to claim 1 formulated for parental, enteral, or oral administration to host.

11. A process for the preparation of a substantially pure complex according to claim 1 which process comprises covalently coupling the carrier molecule to the immunogen by chemical means.

12. A process according to claim 11 wherein the process comprises one or more of the following steps:

a) reacting the immunogen with the carrier to form said complex;

b) chemically modifying the immunogen to provide at least one functional group capable of forming a chemical linkage, and reacting the modified immunogen and carrier to form said complex;

c) chemically modifying the carrier to provide at least one functional group capable of forming a chemical linkage and reacting the immunogen and modified carrier to form said complex;

d) chemically modifying the immunogen and the carrier to provide functional groups capable of forming a chemical linkage, and reacting the modified immunogen and modified carrier to form said complex;

e) reacting the immunogen with at least one linking agent and reacting the linked immunogen and the carrier molecule to form said complex;

f) reacting the carrier with at least one linking agent and reacting the immunogen and linked carrier to form said complex;

g) reacting the immunogen and carrier with at least one linking agent and reacting the linked immunogen and linked carrier to form said complex.

13. The process according to claim 12 which process comprises:

(i) chemically modifying an immunogen to provide at least one functional group capable of forming a chemical linkage; and (ii) reacting the modified immunogen and the carrier to form said complex.

14. A process for the preparation of a complex according to claim 1 in a form adapted for parenteral, oral, or enteral administration to a host which process comprises:

preparing the complex and adding it to a pharmaceutically acceptable diluent.

15. A process for preparing a hybrid protein according to claim 9, comprising:

culturing a host cell expressing said hybrid protein on the surface of said host cell, and purifying said hybrid protein, wherein said hybrid protein comprises an immunogen and a carrier, said carrier comprising TraT.

16. A method for enhancing tile immune response to an immunogen, comprising administering to said host a composition comprising (i) a substantially pure complex comprising said immunogen covalently coupled to a carrier molecule comprising a TraT protein, wherein said immunogen is selected from the group consisting of an antigen and a hapten, and (ii) a pharmaceutically acceptable diluent.

* * * * *